United States Patent
Paulus et al.

[11] Patent Number: 5,739,414
[45] Date of Patent: Apr. 14, 1998

[54] SENSOR WITH GLASS SEAL

[75] Inventors: Nancy Jean Paulus, Grand Blanc; Richard William Duce, Flushing; Sara Ann Touse-Shunkwiler, Grand Blanc; Robert Gregory Fournier, Burton, all of Mich.

[73] Assignee: General Motors Corporation, Detroit, Mich.

[21] Appl. No.: 600,136

[22] Filed: Feb. 12, 1996

[51] Int. Cl.$^6$ .................................................. G01N 27/04
[52] U.S. Cl. .......................................... 73/23.31; 73/31.05
[58] Field of Search .......................... 73/23.31, 23.32, 73/31.05, 31.06; 204/424, 426; 338/34

[56] References Cited

U.S. PATENT DOCUMENTS

| | | | |
|---|---|---|---|
| 3,959,765 | 5/1976 | Stewart | 338/34 |
| 4,282,080 | 8/1981 | Muller et al. | 204/195 |
| 4,310,401 | 1/1982 | Stahl | 204/426 X |
| 4,403,207 | 9/1983 | Murphy et al. | 338/34 |
| 4,462,891 | 7/1984 | Lawless | 204/427 |
| 4,559,126 | 12/1985 | Mase et al. | 204/425 |
| 4,574,042 | 3/1986 | Shiraishi | 204/426 |
| 4,980,044 | 12/1990 | Ker | 204/426 |
| 5,228,975 | 7/1993 | Yamada et al. | 204/424 |
| 5,329,806 | 7/1994 | McClanahan et al. | 73/31.05 |
| 5,467,636 | 11/1995 | Thompson et al. | 73/23.31 |
| 5,490,412 | 2/1996 | Duce et al. | 73/23.31 |
| 5,602,325 | 2/1997 | McClanahan et al. | 73/23.31 |
| 5,616,825 | 4/1997 | Achey et al. | 73/23.31 |

*Primary Examiner*—Hezron E. Williams
*Assistant Examiner*—Daniel S. Larkin
*Attorney, Agent, or Firm*—Anthony Luke Simon

[57] ABSTRACT

A sensor with a glass seal between a planar sensing element in a tubular housing and the tubular housing, wherein the glass seal is maintained in radial compression over an entire temperature operating range of the sensor. The compressed seal has improved strength and durability, is self-limiting and is operable over a large temperature range and in an environment subject to jarring and vibrations.

5 Claims, 6 Drawing Sheets

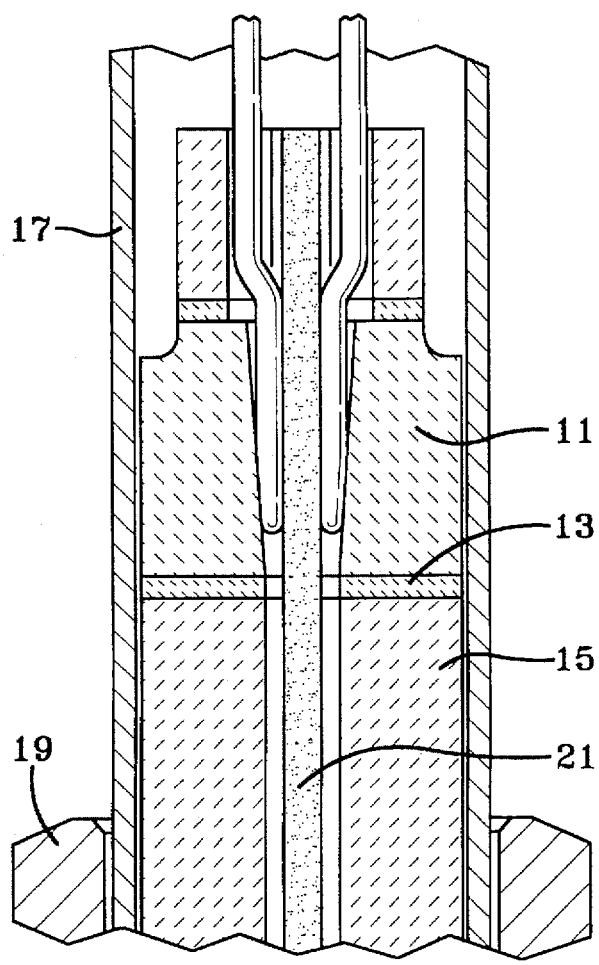
FIG-1
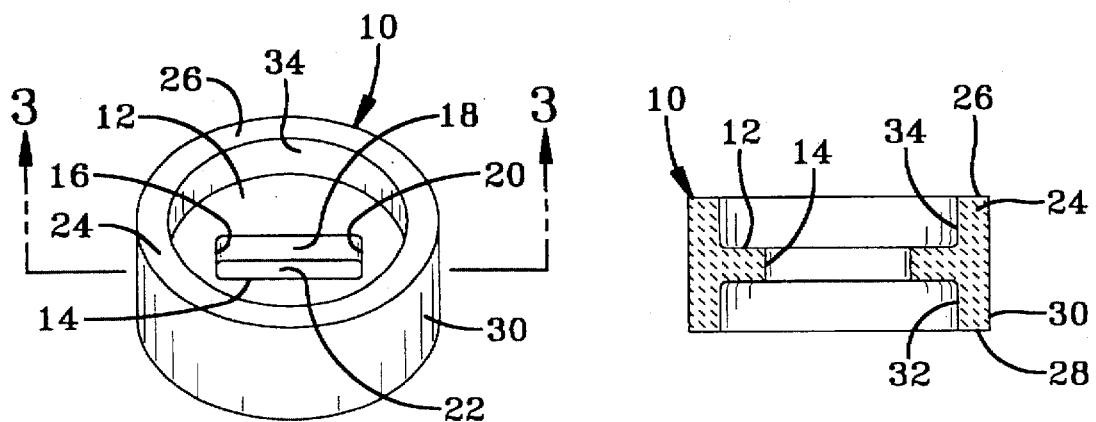
FIG-2
FIG-3

SENSOR WITH GLASS SEAL

This invention relates to a sensor with a glass seal apparatus and method of manufacture.

BACKGROUND OF THE INVENTION

Example glass sealing methods for an oxygen sensor are set forth in U.S. Pat. No. 5,329,806, assigned to the assignee of this invention. In sensors such as in the '806 patent, the purpose of the glass seal is to isolate an end portion of an oxygen sensor from an air reference channel within the sensor. The seal prevents the gas being sensed, i.e., automotive exhaust gas, from leaking into and interfering with the air reference in the channel and the detrimental effect on the measurement output of the sensor that would result from such a leak.

In some prior attempts at achieving the glass seal, the glass seal has been implemented as both a structural and sealing element. Such seals have been prone to failures, including structural cracks allowing leakage into the air reference channel, failure of the glass to adhere to the outer housing of the sensor, and failure to maintain an effective seal over a wide operating temperature range such as required by an exhaust gas oxygen sensor.

Additionally, there is a chance that the sealing glass will see temperatures in excess of the glass transition temperature, in which case the region between the glass sensor and the shell of the sensor is in tension, impairing the structural integrity of the seal. Leaving the glass in tensile stress can lead to cracking in the seal, which allows infiltration of the sensed gas, i.e., automotive exhaust, into the air reference channel.

SUMMARY OF THE PRESENT INVENTION

It is an object of this invention to provide a sensor with a glass seal in accordance with claim 1.

Advantageously, this invention provides a sensor with a glass seal capable of sealing a flat plate sensing element within a circular sensor housing.

Advantageously, this invention provides a new sensor and glass seal that prevents exhaust and other external elements from contaminating the air reference channel in the sensor.

Advantageously, this invention provides a sensor with a glass seal that can be used to seal a planar sensing element in either a ceramic or a metal sensor housing.

Advantageously, this invention provides a sensor with glass seal in which the glass seal coefficient of thermal expansion, transition temperature and melting point are all controlled to maintain a compressive seal within the housing of the sensor allowing the seal to maintain integrity at maximum exhaust sensor service temperatures. Accordingly, this invention provides a sensor with glass seal in which the glass seal is in compression during the entire operating range of the sensor, maintaining a glass to metal or ceramic seal.

Advantageously, according to this invention, a glass to metal seal is maintained by providing a seal with a coefficient of thermal expansion in a range equal to the coefficient of thermal expansion of the sensing element and less than the coefficient of thermal expansion of the metal sensor shell wherein the metal sensor shell holds the glass in compression, allowing the glass seal to maintain its maximum strength over the entire operating range of the sensor. Advantageously, by maintaining the glass seal in compression, the seal according to this invention can withstand conditions of shock and vibration in an engine environment and has improved mechanical integrity.

Advantageously, an example sensor with glass seal according to this invention is achieved with a glass seal having a flat circular disk portion, including a centrally located rectangular opening in which a planar sensing element is located. At an outer radial periphery of the flat disk portion, the seal forms a circular cylindrical wall extending axially away from the flat circular disk portion in first and second directions opposite to each other. The seal is placed within the sensor housing wherein the circular cylindrical wall engages the inner cylindrical wall of the sensor housing and wherein the rectangular opening engages the planar sensing element. The seal is located between first and second insulators that act to structurally locate the seal and sensor element. The outer cylindrical surface of the seal bonds with the circular wall of the sensor housing and the rectangular opening of the seal bonds with the sensing element, wherein the seal seals a first end of the sensing element in a sensing chamber from a second end of the sensing element in an air reference channel in the sensor. In one example, the flat circular disk portion has a thickness less than the thickness of the planar sensing element.

Advantageously, then, in one example this invention provides a method of manufacturing a sensor with a glass seal, comprising the steps of: placing a glass seal having a circular disk portion with a rectangular opening centrally located therein and an annular cylindrical wall extending first and second axial directions from a periphery of the circular disk portion into a sensor housing wherein an outer cylindrical surface of the annular cylindrical wall of the seal is proximate to an inner cylindrical wall of the housing and wherein a sensing element passes through the rectangular opening in the circular disk portion of the seal; heating the sensor package to a temperature at which the glass of the seal melts, wherein the annular cylindrical wall of the seal melts and flows to the inner cylindrical wall of the shell and wherein glass around the perimeter of the sensing element flows around the sensing element; and cooling the sensor, wherein said glass cools and maintains a seal between the sensing element and the outer shell of the sensor.

BRIEF DESCRIPTION OF THE DRAWINGS

The present invention will now be described by way of example with reference to the following drawings in which:

FIG. 1 illustrates a first example sensor and glass seal according to this invention;

FIGS. 2 and 3 illustrate an example glass seal according to this invention;

DETAILED DESCRIPTION OF THE INVENTION

EXAMPLE 1

Figure 4:
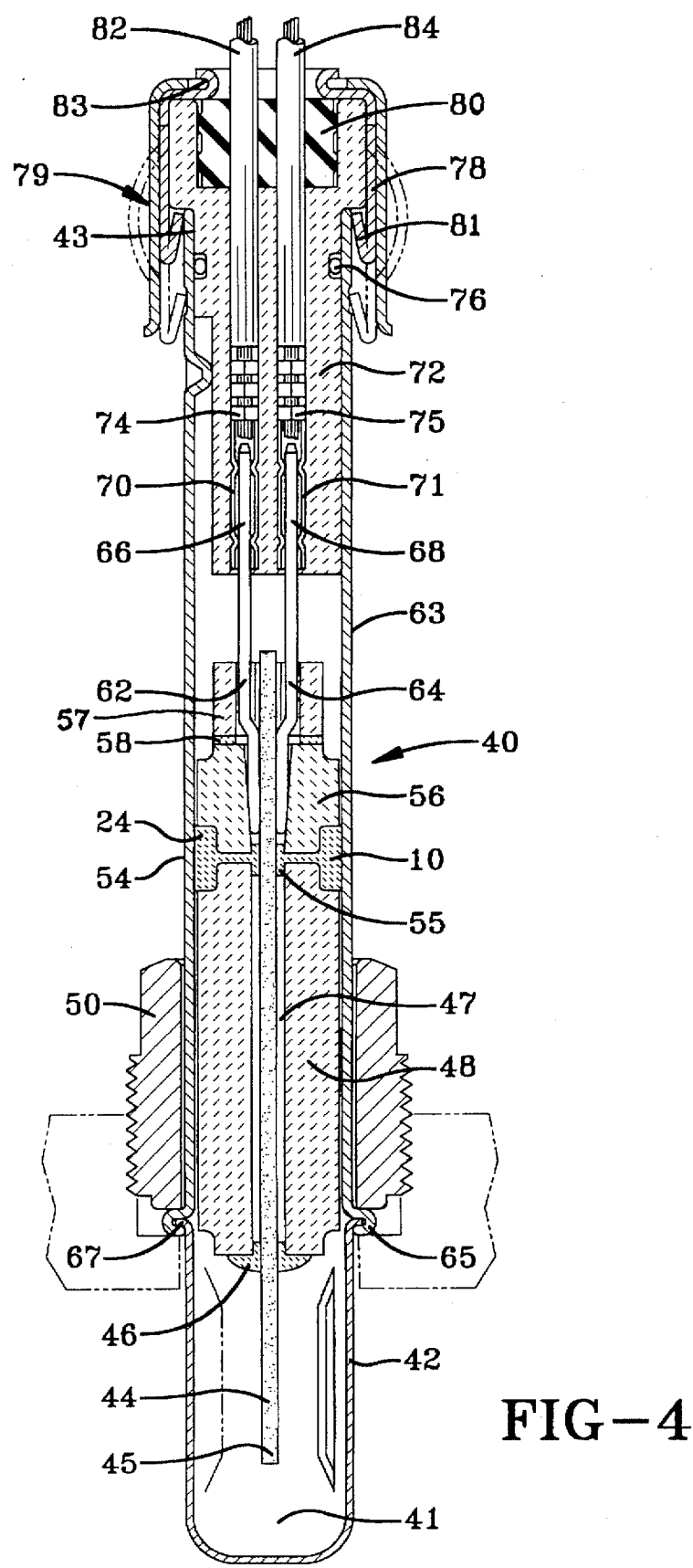
FIG. 4 illustrates a second example sensor with glass seal according to this invention.

In a first example, a glass seal in a sensor is achieved by reducing the thickness of the seal designated as reference 48 in FIG. 3 of the above mentioned U.S. Pat. No. 5,329,806 so that it is thinner than the planar sensing element or on the order of about one millimeter or less. Referring to FIG. 1, the glass seal 13 according to this invention is provided with a central opening rectangular in shape to match the shape of the planar sensing element 21, which extends through the opening. On either side of the seal 13, then, are placed two insulators 11 and 15 of steatite glass having melting temperatures higher than that of the seal. The sensor is treated in a furnace to melt and flow the glass of the seal to engage the inner cylindrical wall of the sensor housing (outer shell) 17 and the outer surface of the planar sensing element 21. The sensor is then cooled so that the glass hardens, sealing the sensor within the housing and providing an air tight seal separating the first and second ends of the sensor.

The furnace treating of the sensor must be maintained for a time sufficient to allow the glass of the seal 13 to flow out to meet the sensor housing 17. Special care must be taken to maintain pressure on the seal 13 perpendicular to the seal as pressure provided at an angle can cause irregular flow of the glass and the possibility of leaving an air gap between the seal and the shell of the sensor.

To prevent the glass from deforming the sensor housing 17 during the cooling step, the yield strength of the sensor housing must be great enough so that the housing maintains the glass in compression and does not yield to the glass. If the housing 17 yields to the seal 13, the housing 17 becomes deformed around the seal and, during operation at high temperatures, the housing expands, placing the seal in tension, leading to failure of the sealing bond between the glass and the housing and/or cracks in the seal, resulting in an imperfect seal. A housing 17 with appropriate yield strength may be achieved by providing a thick enough wall of the housing 17 and/or by appropriate selection of material, i.e., 0.018"–0.024" thick SAE 486 stainless steel.

The fitting 19 is mounted around the housing 17 and is used for mounting of the sensor as described below.

EXAMPLE 2

Referring now to FIGS. 2 and 3, a preferred example glass seal according to this invention is designated by reference 10 and generally comprises a circular shaped flat disk portion 12 having centrally located therein an opening 22 defined by walls 14, 16, 18, and 20 for engaging a planar sensing element having a shape substantially matching that of the opening 22. Preferably the thickness of the flat disk portion 12 is less than the thickness of the planar sensing element and, in one example, is on the order of one millimeter. At the radial periphery of the flat disk portion 12, the seal 10 has an annular cylindrical wall 24 extending axially away from the flat circular disk portion 12 in both directions so that the flat circular disk portion 12 is substantially centrally located within the cylindrical tube formed by the cylindrical wall 24. In one example, the cylindrical wall 24 has an axial length of 4 mm and a thickness of between 0.5 and 1.0 mm.

The cylindrical wall 24 has a top annular end 26 and a bottom annular end 28, inner annular cylindrical surfaces 34 and 32 and an outer cylindrical surface 30. When the sensor is constructed with the seal 10 shown, the outer cylindrical surface 30 bonds to a sensor housing and the inner peripheral walls 14, 16, 18, and 20 of the opening 22 bond to a sensing element to seal a first end of the sensing element in a chamber exposed to a gas to be sensed, i.e., vehicle exhaust gas, away from a second end of the sensing element in an air reference channel.

FIG. 4 illustrates an example sensor with glass seal according to this invention. The sensor 40 generally comprises an outer housing comprising lower shell 42 and upper shell 63 formed from a material such as 486 steel having a coefficient of thermal expansion in the range of $11 \times 10^{-6}$ to $12 \times 10^{-6}/°$ C. Upper shell 63 has a peripheral fold 65 around the lip 67 of the lower shell 42, joining the upper and lower shells 63 and 42 together. Annular fitting 50 fits around shell 63 above fold 65. The fitting 50 is adapted to mate with a receptacle for mounting the sensor 40 in a gas flow path.

Sensing element 44, constructed in a manner known to those skilled in the art, such as described in U.S. Pat. No. 5,329,806, assigned to the assignee of this invention, is generally a flat planar sensing element having an end 45 exposed to exhaust gases in chamber 41 for sensing the oxygen content of the exhaust gases therein. A glass support 46 locates the sensing element 44 within the axial opening 47 of insulator 48. Insulator 48 is formed, for example, from a steatite type material having the characteristics of low thermal conductivity. During sensor operation, gases entering chamber 41 may be of temperatures as high as 950° to 1000° C. The insulator 48 insulates the glass seal 10 from such high temperatures and the glass seal 10 never sees temperatures higher than the glass transition temperature, which, in this example, is approximately 720° C. Typically, the highest temperature that glass seal 10 reaches during normal sensor operation is 650° C.

The glass seal 10 is shown located between insulator 48 and insulator 56, which is formed of alumina and has a coefficient of thermal expansion similar to insulator 48. A third insulator 57 is connected by glass 58 above insulator 56. The seal 10 has been heated and bonded to both the sensing element 44 and the outer shell 42 of the sensor in the region 54.

More particularly, during the furnace heating of the sensor, the glass seal 10 melts and, through capillary action, flows a small distance in the axial direction along the sensing element 44 as shown by reference 55. When the sensor is cooled, the glass is bonded to the sensing element 44. Also during the heating process, the cylindrical wall 24 of the seal 10 flows into contact with the inner periphery of shell 63 in the region 54 so that when the sensor is cooled, the glass is bonded thereto. The cylindrical wall 24 provides material to flow and meet the shell 63, eliminating the reliance on capillary action to draw the glass axially along the periphery of the shell 63 in the region 54 to form a sealing bond, which in turn does not cause a build up of tension along the shell.

Shell 63 has a coefficient of thermal expansion greater than that of the glass seal 10. For example, the glass seal 10 may comprise a Sr borosilicate glass with a coefficient of thermal expansion of $7.8 \times 10^{-6}/°$ C. As a result, the shell 63 expands faster than the glass of the seal 10 during the furnace heating and treatment. However, because the cylindrical portion 24 provides sufficient material to flow out to meet the region 54 of the shell 63, the greater coefficient of thermal expansion of shell 63 does not adversely affect the sealing capability of the glass seal 10. Rather, because the glass flows out to meet the expanded shell in the region 54, as the sensor cools and the shell contracts, the glass seal 10 solidifies and then enters into a state of compression being compressed by the shell 63 in the region 54. This state of compression strengthens the seal as glass is inherently stronger under compression. Further, this process eliminates the possibility of the glass seal 10 undergoing tension during operation of the sensor since the glass seal region of the sensor is at an operating temperature range below the temperature at which the glass seal melts. Thus, in an exhaust environment where chamber 41 of the sensor is typically exposed to temperatures in the range of –40° to +1000° Celsius, the glass seal 10 region is maintained in compression and therefore in a state of structural integrity since it never sees a temperature greater than the glass transition temperature.

Additionally, the planar sensing element has a coefficient of thermal expansion equal to that of the glass, preventing the glass around the planar sensing element from undergoing tension. An example coefficient of thermal expansion of the planar sensing element is $8 \times 10^{-6}/°$ C.

Figure 5:
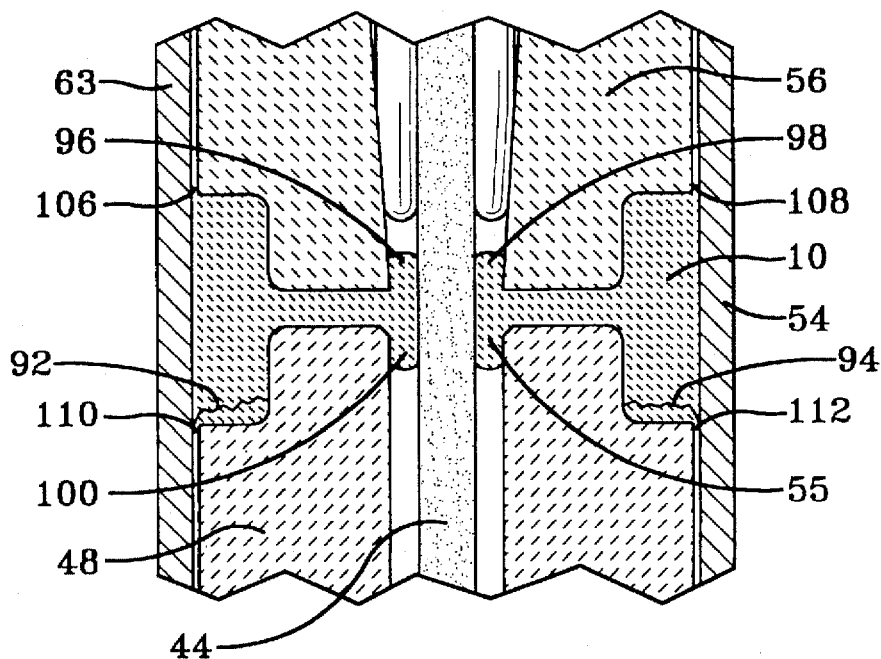
FIG. 5 illustrates example benefits of the sensor with glass seal according to this invention.

Referring to FIG. 5, small portions of the outer periphery of the cylindrical wall of the glass seal 10 may, through capillary action, flow axially between insulator 48 and shell 63 or insulator 56 and shell 63 and such portions 106, 108, 110, and 112 may end up in tension. However, as shown with reference to FIG. 5, cracks (92 and 94) that may develop due to the tension in the capillary flow areas inherently turn while propagating to dead end against the insulator 48 or 56 on the same side from which the crack started. The cracks thus become self limiting and do not translate across the seal 10 to form leak paths for exhaust gas into the air reference chamber. These results have been verified by experimentation and analysis of sample sensors according to this invention.

During the furnace treatment, portions of the glass 96, 98, 100, and 55 are drawn axially through capillary action to help seal around sensing element 44.

Referring again to FIG. 4, the remainder of the sensor includes the terminals 62 and 64 bonded to the sensing element 44 in a known manner and terminating in male terminal ends 66 and 68, which engage female receptacles 70 and 71 of the connector 79. The female receptacles 70 and 71 are tubular shaped metal receptacles constructed in a manner known to those skilled in the art and are crimped (at 74 and 75) to wires 82 and 84 for electrical connection in a known manner. The receptacles 70 and 71 are retained in the insulator 72, which is sealed by O-ring seal 76 to the end 43 of the shell 63.

Connector 79 has an outer shell 78 including a cantilever retaining feature 81 for maintaining the shell and connector 79 on the end 43 of the sensor shell 63. The end of the connector includes a floral elastomer seal 80 for maintaining the wires in place and for sealing against water contamination from outside the sensor. The end of the outer shell 78 is folded as shown by reference 83, maintaining the insulator 72 in place.

Figure 6:
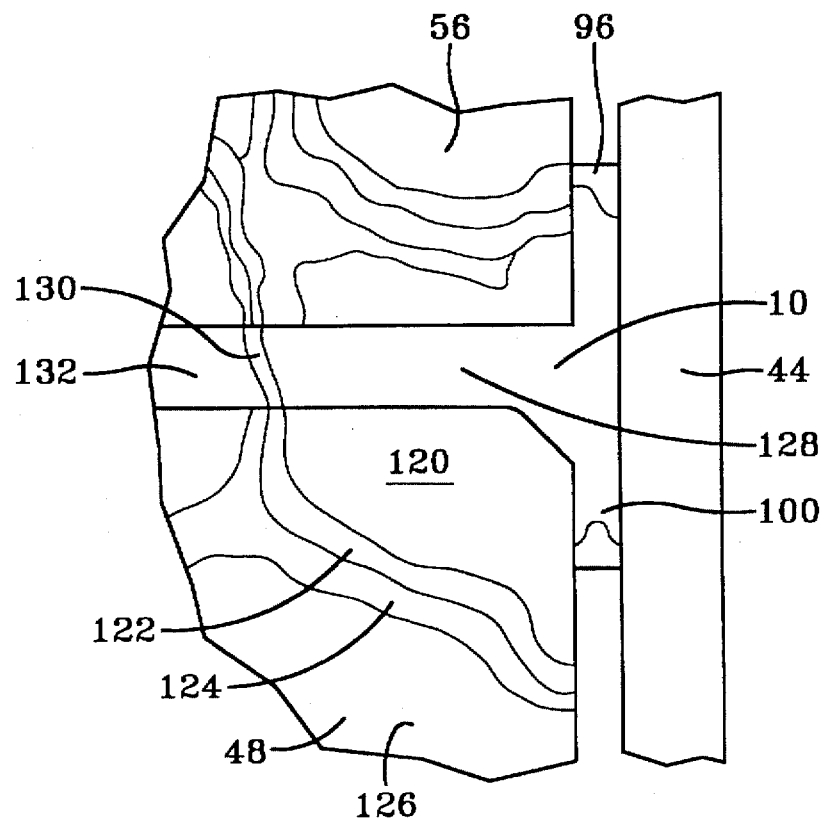
FIG. 6 illustrates a stress analysis of the sensor with glass seal according to this invention.

Referring to FIG. 6, the example stress analysis shown illustrates the positive pressure on the glass seal 10 due to the seal structure, including the cylindrical walls 24 according to this invention. The structure shown illustrates compressive stress on the glass seal 10 in an example operating temperature of −40° Celsius, which is the lowest expected operating temperature of the example sensor shown and the temperature at which the glass seal experiences the greatest amount of compressive stress along the shell region, increasing slightly across the seal region toward the element by approximately 30 MPa. The portions of the seal and insulators designated by references 128 and 120, respectively, have the highest compressive stress, peaking at −93.11 MPa. The regions (122, 124, and 126) and (130 and 132) illustrate gradually reduced stress regions in the ceramic component in an area just below the seal region.

The figure illustrates the compressive stress profile of the seal 10 under the condition of greatest stress and the structural integrity of the seal under such conditions that allow the seal 10 to be an effective mechanical structure while maintaining the glass to metal seal. Because of the high compressive stress level of the glass 10, the glass seal 10 can now maintain integrity in the environment of the vehicle engine where exposure to vibrations and wide operating temperature ranges is common.

EXAMPLE 3

Figure 7:
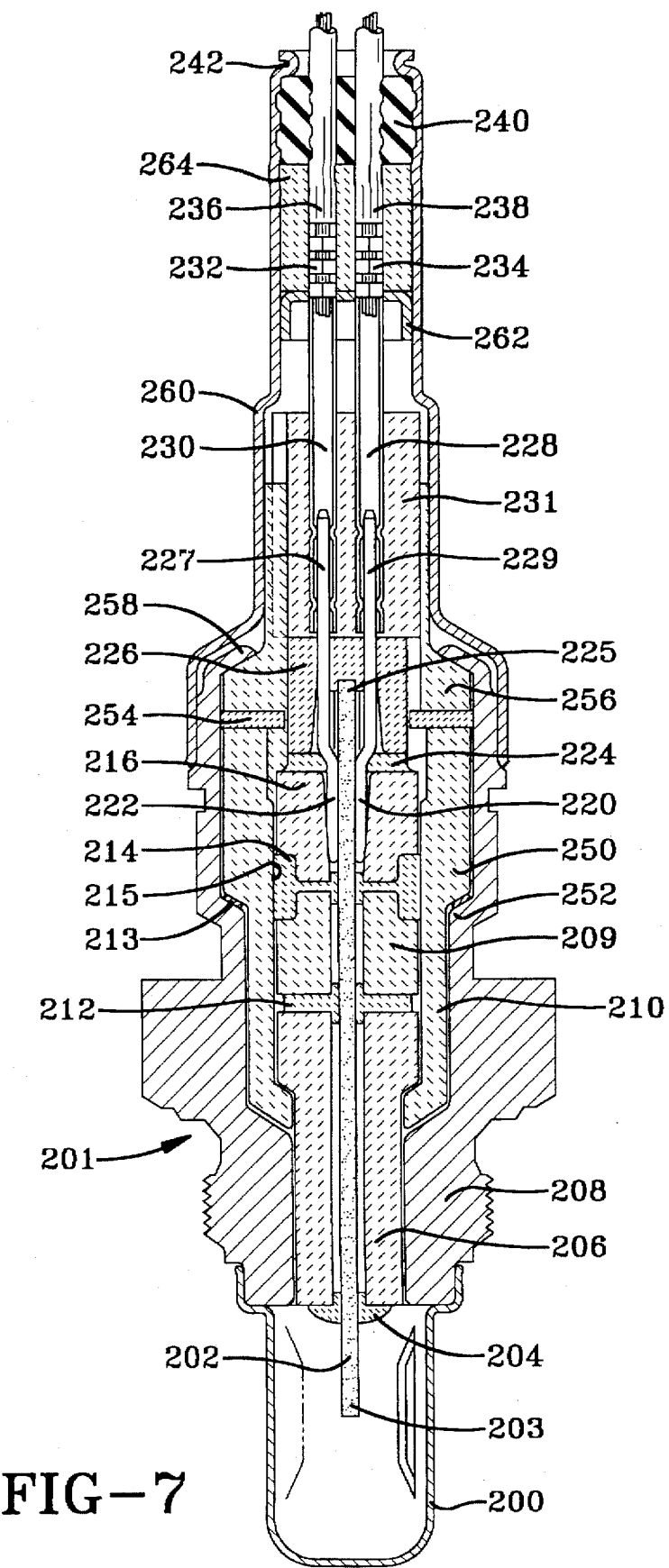
FIG. 7 illustrates a third example sensor with glass seal according to this invention.

Referring now to FIG. 7, another example sensor with a glass seal according to this invention is shown. In the example shown in FIG. 7, the glass seal 214 seals between a tubular ceramic insulator 210 and the planar sensing element 202 in much the same way that the seal 10 in FIG. 4 seals between the metal shell and planar sensor 44.

More particularly, the sensor 201 shown comprises a lower shield 200 attached to a steel fitting 208 and provides a chamber for exposure of exhaust gas to the end 203 of the planar sensing element 202. A glass support 204 maintains the sensing element 202 in place with respect to lower insulator 206 comprising a steatite material similar to lower insulator 48 in FIG. 4. The glass support 204 also shortens the cantilever of the element with respect to the package. An intermediate glass spacer 212 is provided between lower insulator 206 and middle insulator 209. The glass seal 214 according to this invention, similar to glass seal 10 described above, is provided between the middle insulator 209 and the upper insulator 216 as shown. An example material for the glass seal 214 is Ba borosilicate having a coefficient of thermal expansion in the range of $5 \times 10^{-6}$ to $7 \times 10^{-6}/°$ C. The annular cylindrical wall of the seal 214 interfaces with the inner cylindrical wall 215 of the ceramic insulator 210 (the housing). During a furnace heating process similar to that described above with respect to FIG. 4, the material of the glass from the cylindrical outer wall of the seal 214 flows into contact with the ceramic insulator 210. The ceramic insulator 210 has a coefficient of thermal expansion greater than or equal to that of the glass seal 214. During cooling, the glass solidifies, bonding with ceramic insulator 210, providing a seal between the glass seal 214 and the ceramic insulator 210.

As with the sensor with the steel shell 63 above with respect to FIG. 4, after the furnace heating, when the sensor has cooled, the seal 214 is solidified in sealing contact with the ceramic insulator 210 and the sensing element 202. The resulting glass seal 214 is in compression similar to the way that seal 10 is in compression in FIG. 4, guaranteeing the integrity of the seal and preventing the flow of exhaust from the end 203 of the sensing element 202 to the air reference channel near end 225 of sensing element 202.

The ceramic insulator 210 is mounted within the steel body 208 that comprises the fitting for the sensor and a seal is provided between the ceramic insulator 210 and the steel body 208 by gasket 213 between the shoulders 250 and 252 of the ceramic insulator 210 and steel body 208, respectively. A disk spring 254 is provided between the upper end of the ceramic insulator 210 and the insulating spacer 256, providing pressure on the ceramic insulator 210 maintaining sealing compression of the gasket 213. The insulating spacer 256 is held in place by the crimp 258 on the upper end of the steel body 208.

In the wedge opening of the upper insulator 216, terminals 220 and 222 are attached to the sensor element 202 in a known manner. Terminals 220 and 222 extend upward and form male terminal ends 227 and 229 engaging female receptacles 230 and 228 within insulator 231. Spacer 226 and glass 224 are located between insulator 231 and upper insulator 216. The upper end of the sensor 201 is enclosed in the steel shell 260, crimped to the outer periphery of the steel body 208, enclosing the terminal end of the sensor. The female receptacles 230 and 228 include crimped ends 232 and 234 located within insulator 264 for engaging the wires 236 and 238 providing electrical connection to the sensor 201. The wires 236 and 238 pass through viton seal 240, which is maintained in place by the crimped end 242 of the shell 260. Within the upper shell 260, a metal retainer 262 is fit in place, for example by a friction fit, to provide a positive locating stop of the insulator 264.

Figure 8:
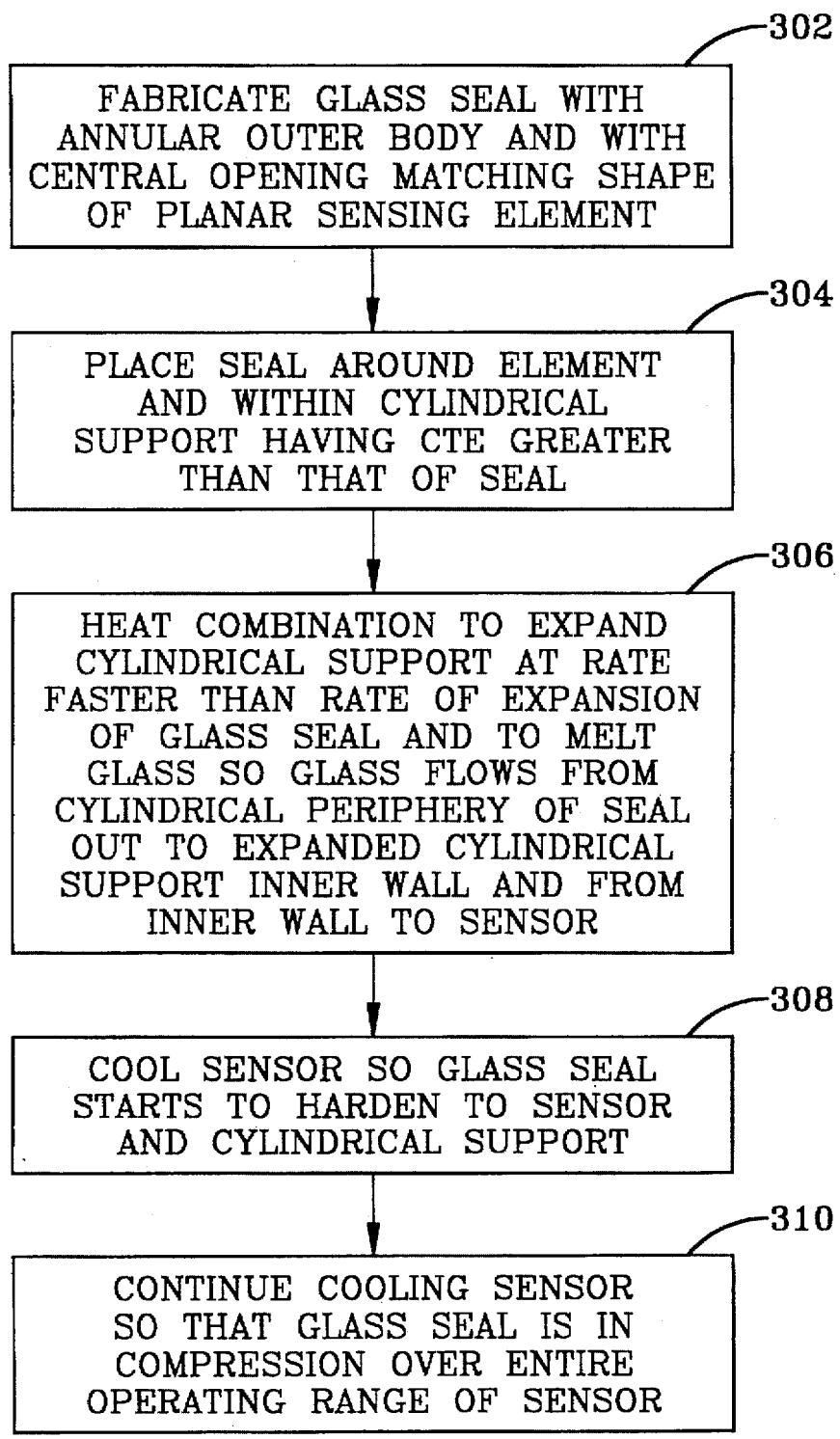
FIG. 8 illustrates the method according to this invention.

Referring now to FIG. 8, an example method of manufacturing a sensor with a glass seal according to this invention is shown. At step 302, the glass seal 10 (FIGS. 2–4) is fabricated to include an annular outer body and a flat disk portion with a central opening matching the shape of a planar sensing element 44 (FIG. 4). At step 304, the glass seal is placed around the planar sensing element so that the planar sensing element passes through the opening and the combination is placed in a cylindrical support (shell 42, FIG. 4) having a coefficient of thermal expansion greater than that of the glass of the seal (block 304). The combination is then heated (block 306) to expand the cylindrical support at a rate faster than the rate of expansion of the glass seal and to melt the glass of the glass seal so that the glass flows from the annular outer body of the seal out to the expanded cylindrical support inner wall and from the periphery of the central opening to the planar sensing element. The combination is then cooled so that the glass seal hardens in a state bonded to the sensing element and to the cylindrical support (block 308). The cooling of the combination is continued (block 310) so that the glass seal is in compression over the entire operating range of the sensor. The result is a sensor with a robust glass seal sealed to both the planar sensing element and the cylindrical support.

Figure 9:
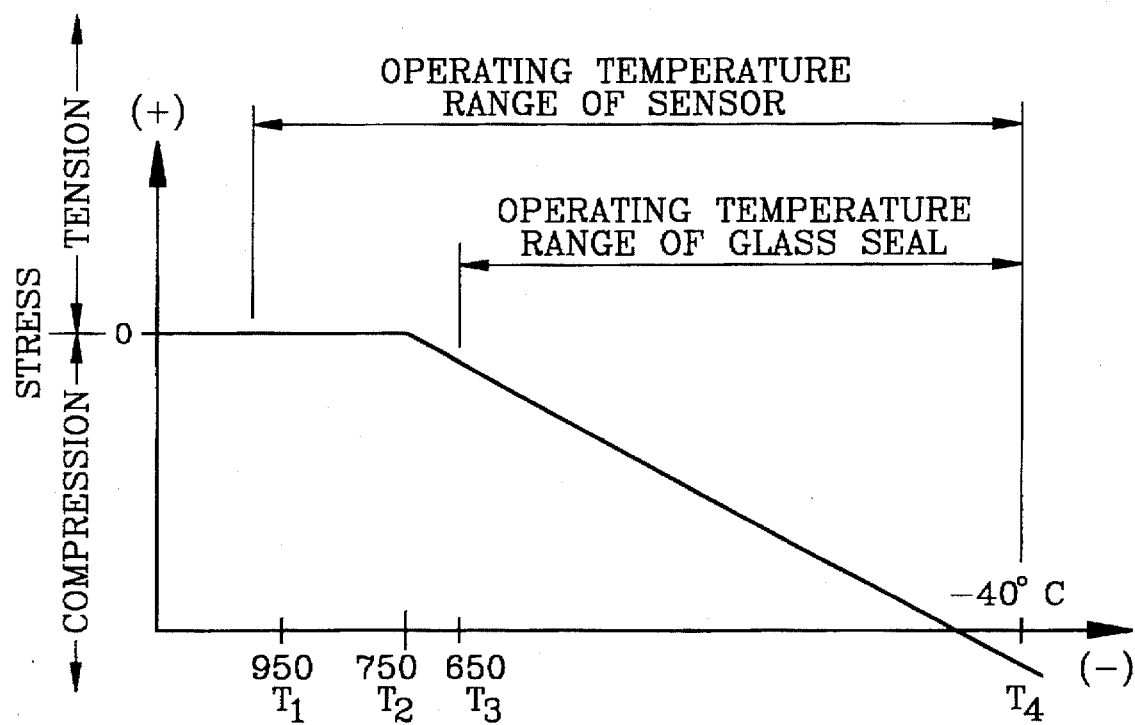
FIG. 9 illustrates the operation of this invention.

FIG. 9 illustrates the relationship between the sensor design, manufacture, and characteristic compression of the seal. The horizontal axis illustrates temperature, which is increasing to the left, and the vertical axis illustrates stress on the seal. When the sensor is heated during manufacture to a temperature $T_1$ (for example 950° C.) greater than the highest operating temperature of the glass seal region of the sensor, the glass seal becomes fluid and glass from the outer cylindrical wall of the seal flows out to come in contact with the inner cylindrical wall of the sensor housing. At this temperature, the housing is expanded due to its high coefficient of thermal expansion. Because the glass is fluid there is substantially zero stress on the glass seal.

As the sensor is cooled, the glass seal 10 solidifies at temperature $T_2$ (for example 750° C.), bonding to the temperature expanded sensor housing or shell. As the sensor is continuously cooled, the sensor housing contracts at a rate greater than that of the glass seal. This causes the stress on the glass seal to fall below zero, maintaining the glass seal in compression between its upper and lower operating temperatures $T_3$ (for example 650° C.) and $T_4$ (for example −40° C.), with the compressive stress increasing as the operating temperature of the glass seal region of the sensor decreases. By ensuring solidification and bonding of the seal to the housing while the housing is above the maximum operating temperature, the seal is maintained in compression over the entire operating temperature of the sensor.

EXAMPLE 4

Figure 10:
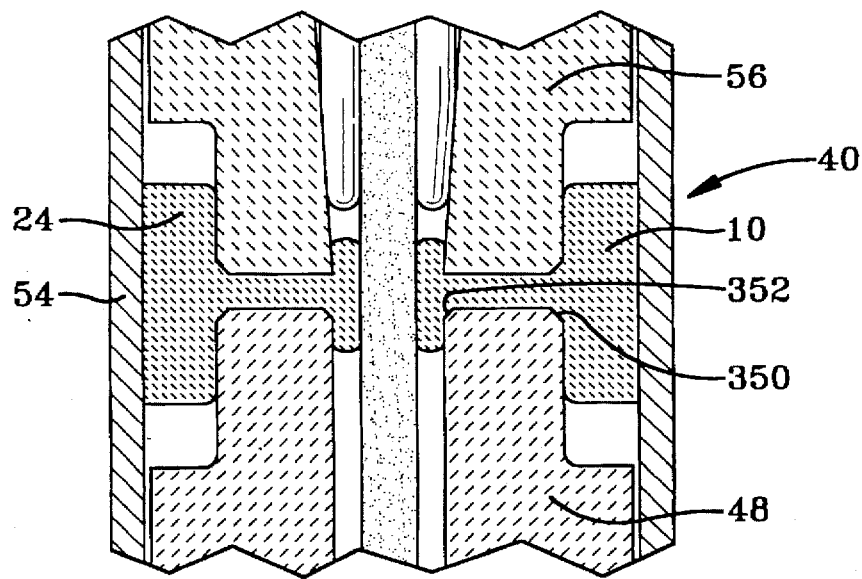
FIG. 10 illustrates another example of this invention.

FIG. 10 illustrates another example sensor according to this invention, similar to the example shown in FIG. 4 with the addition of chamfers 350 and 352 on the top edge of the lower insulator 48. The chamfer 350 extends entirely around the periphery of the top outer edge of insulator 48 and the chamfer 352 extends entirely around the top inner edge of the insulator 48 proximate to the sensing element 44. The sensor 40 implemented with the chamfers 350 and 352 on insulator 48 exhibits good performance of the seal 10.

We claim:
1. A sensor comprising:
   a tubular housing:
   a planar sensing element axially within the tubular housing; and
   a glass seal between an exterior periphery of the planar sensing element and an interior periphery of the tubular housing, wherein the tubular housing has a first coefficient of thermal expansion greater than a second coefficient of thermal expansion of the glass seal, wherein the second coefficient of thermal expansion of the glass seal is similar or equal to a third coefficient of thermal expansion of the planar sensing element, wherein the glass seal is maintained in radial compression over an entire temperature operating range of the sensor and wherein cracks that form in the glass seal propagate to self limit and do not translate across the glass seal to form leak paths.

2. A sensor according to claim 1, wherein the glass seal comprises a circular disk portion and an annular cylindrical wall portion at an outer radial periphery of the flat circular disk portion extending axially away from the flat circular disk portion in first and second directions opposite to each other, wherein the annular cylindrical wall portion is in sealing contact with the tubular housing.

3. A sensor according to claim 2, wherein the glass seal also comprises a rectangular opening in sealing engagement with the planar sensing element.

4. A sensor according to claim 1, also including first and second cylindrical insulators on first and second axial sides of the glass seal within the tubular housing, wherein the planar sensing element passes through the first and second cylindrical insulators, wherein the first and second cylindrical insulators are in contact with the glass seal, wherein at least a first portion of the first cylindrical insulator in contact with the glass seal is in compression and at least a second portion of the second cylindrical insulator in contact with the glass seal is in compression.

5. A sensor according to claim 1, wherein the glass seal has a circular disk portion with a first thickness less than a second thickness of the planar sensing element.

* * * * *